United States Patent [19]
Khartchenko et al.

[11] Patent Number: 5,871,695
[45] Date of Patent: Feb. 16, 1999

[54] DIAGNOSTIC STRIPS

[75] Inventors: Serguei V. Khartchenko; Nadejda P. Khartchenko; Alissa S. Khartchenko; Alina S. Khartchenko, all of Edmonton, Canada

[73] Assignee: New Diatech Diagnostic Technology Corp., Victoria, Canada

[21] Appl. No.: 571,046

[22] Filed: Dec. 12, 1995

[51] Int. Cl.$^6$ .................................................. G01N 33/48
[52] U.S. Cl. ................................ 422/56; 422/61; 422/58; 436/169
[58] Field of Search ................................ 422/56, 58, 61; 436/169

[56] References Cited

U.S. PATENT DOCUMENTS

| | | | |
|---|---|---|---|
| 3,348,920 | 10/1967 | Ferro et al. | |
| 3,912,457 | 10/1975 | Ogawa et al. | |
| 3,992,158 | 11/1976 | Przybylowicz et al. | 422/58 |
| 4,007,258 | 2/1977 | Cohen et al. | 424/22 |
| 4,740,393 | 4/1988 | Cody et al. | 427/388.1 |

FOREIGN PATENT DOCUMENTS

| | | |
|---|---|---|
| 2072423 | 12/1993 | Canada . |
| 0475045 | 3/1992 | European Pat. Off. . |
| 9202133 | 2/1992 | WIPO . |

OTHER PUBLICATIONS

The Aldrich Chemical Company Catalog, p. 743, 1988.

*Primary Examiner*—Lyle A. Alexander

[57] ABSTRACT

A gelatinous reagent containing chloride ions, aliphatic alcohol, $Fe^{3+}$ and trace amounts of selected agents is useful for detecting the pathologies of atherogenic metabolism and bilirubinemia by observation of a color change when the reagent is brought into contact with a body fluid. The reagent can be carried on a diagnostic strip or can be used for spectrometric analysis in liquid form. The reagent can be used with a second reagent containing oxammonium sulfate to identify the pathologies by measurement of the electro-potential generated when a body fluid is brought into contact with both of the reagents.

6 Claims, 4 Drawing Sheets

DIAGNOSTIC STRIPS

FIELD OF THE INVENTION

This invention relates to diagnostic strips and, in particular, diagnostic strips for detecting atherogenic metabolic abnormalities or bilirubinemia and methods of use.

BACKGROUND OF THE INVENTION

Atherogenic metabolism leads to atherosclerosis and is characteristic of a cellular energy deficiency, by blocked oxidative phosphorylation, negative nitrogen balance and increased proteolysis. Atherogenic metabolism accompanies diabetes mellitus type I and II, essential hypertension (linked to diabetes), chronic sublethal cyanide poisoning, such as by heavy cigarette smoking, acute cyanide poisoning, from fire smoke inhalation, and syndrome X, which is an insulin resistant state that precedes the disorders of diabetes mellitus, hypertension, certain dislipidemias, and premature atherosclerotic vascular disease.

There are two important alternatives to glucose as a fuel: amino acids (from functional protein) and triglycerides (from the body's fat stores). In the disturbed metabolism of diabetes and cyanide toxicity, selective proteolysis of functional intracellular proteins occurs to provide the amino acid precursors for the Krebs cycle, in an attempt to restore energy production which has been incorrectly perceived by the body as starvation.

This proteolytic state is highly atherogenic due to excessive sulphur metabolism (with increased methionine, homocysteine, and cysteine metabolism), and the presence of oxidants and free radicals. It is also associated with the transportation of increased amounts of triglyceride from fat stores. It is precisely this atherogenic proteolytic state which is responsible for 75% of diabetic deaths. It also causes 80% of deaths in individuals with chronic sub-lethal cyanide toxicity and Syndrome-X.

This energy depleted atherogenic, proteolytic state causes activation of the important enzyme glutamine synthetase (GS). GS activity is associated with the disturbed metabolism of diabetes mellitus, heavy smoke inhalation, and essential hypertension where it is linked to non-insulin dependent diabetes mellitus and lipid disturbances such as Syndrome-X. These states share equal importance as major risk factors for atherosclerosis.

When the body is able to metabolize glucose (the diabetic metabolism is adequately corrected, cyanide levels are low and the body is not starved) GS will be substantially inactive. The atherogenic proteolytic state is not present. When the body is unable to metabolize the preferred fuel, glucose, the proteolytic metabolic shift will occur and this will necessitate activation of GS and degradation of thiocyanate.

It is known that normalizing glycemic levels will reduce atherosclerosis in diabetics. It is predicted that better control of the disordered, atherogenic diabetic metabolism earlier in the course of an illness will reduce diabetic deaths caused by atherosclerosis.

Reagents are known for screening and for monitoring such abnormal metabolic conditions. Most reagents focus directly upon the function of the pancreas by monitoring the levels of pancreatic products, such as insulin, within body fluids. Others measure the level of glucose within body fluids. However, these tests can be invasive and are often inadequate to determine atherogenesis. In particular, in these atherogenic disorders it is the energy deficiency of the cells which is of concern. The levels of, for example, glucose and insulin are not directly indicative of this cellular state since these levels can vary in relation to various effects, such as exercise, glucose consumption, insulin antibodies and insulin resistance.

The earliest methods for monitoring cellular energy deficiencies by abnormal glucose and/or lipid metabolism measured protein metabolism by means of a whole body nitrogen balance. However, many problems were associated with these methods as set out in Joslin's Diabetes Mellitus, 1994, p. 118.

A reagent is known as described in published Canadian patent application s.n. 2,072,423 which allows screening for atherogenic metabolic abnormal conditions by observing a color change when the reagent is introduced to saliva. However, this reagent has some disadvantages. For example, a specific ratio of saliva to reagent is required to obtain reproducible and accurate results and there has been difficulty in differentiating between color changes in some lighting conditions. In addition, it has been found that there is not a clear color distinction between a moderate risk condition and an actual pathology.

A test-strip is required which will enable early discovery of atherogenic metabolism. As well, a test is required which can be conducted by untrained, as well as trained, persons.

SUMMARY OF THE INVENTION

A diagnostic strip and method for use has been invented for screening for and monitoring atherogenic metabolism which has significant correlation with cellular energy deficiencies, proteolytic processes and negative nitrogen balance. Such abnormalities can be caused by insulin dependent and non-insulin dependent diabetes mellitus, Syndrome X, vascular disease, hypertension, and cyanide toxicity, for example, by heavy cigarette smoking (i.e. more than 10 cigarettes per day) or fire smoke inhalation. All of these pathologies have a greatly increased risk of atherosclerosis in common. The test strip can be used in clinical or non-clinical environments. The strip is simple to use and is non-invasive requiring contact with saliva in humans or urine in animals for a distinct condition indication.

In one embodiment, the test strip uses a distinct calorimetric reactions to indicate the subject's condition. The color change of the strip resulting from contact of the strip with an appropriate body fluid indicates the degree of the cellular energy deficiency and atherogenic metabolism abnormalities. The strip can also indicate that there exists a significant concentration of bilirubin in the body fluid, for example more than 1 mg/ml, and thereby indicate an occurrence of bilirubinemia.

In another embodiment, the diagnostic test strip contains components which result, when in contact with the body fluids, in an electropotential which indicates the degree of atherogenic metabolism and the condition bilirubinemia.

According to a broad aspect of the present invention there is provided a gelatinous reagent containing about 0.05 to 6.0M chloride ions, about 0.05 to 5.5M aliphatic alcohol, 0.015 to 4.0M $Fe^{3+}$ and at least trace amounts of calcium, sodium, potassium, nitrate, sulfate, phosphate, copper, zinc, $Fe^{2+}$, lead and arsenic.

The reagent can be applied to a carrier for production of a diagnostic strip or can be used for spectrometric analysis.

According to another broad aspect of the present invention, there is provided a diagnostic strip comprising: a first gelatinous reagent containing about 0.05 to 6.0M chloride ions, about 0.05 to 5.5M aliphatic alcohol, 0.015 to 1.85M $Fe^{3+}$ ions and at least trace amounts of calcium, sodium, potassium, nitrate, sulfate, phosphate, copper, zinc, $Fe^{2+}$, lead and arsenic; and a second gelatinous reagent containing about 3.0 to 4.0M oxammonium sulfate, the first and second reagents being closely positioned on the strip.

According to a further broad aspect of the present invention, there is provided a method for detecting atherogenic metabolism or bilirubinemia comprising:

providing the reagent of the present invention in any suitable form contacting the reagent with a sample of a biological fluid; and observing the reagent for a color change or measuring the electropotential.

DESCRIPTION OF THE INVENTION

The strips of the present invention are useful for indicating that a subject is experiencing an atherogenic metabolic abnormality resulting in cellular energy deficiency, proteolytic processes and a negative nitrogen balance by a color or electropotential change of a diagnostic reagent.

It is known that in atherogenic metabolism the body system suffers from a shortage of energy (ATP) by altered glucose metabolism. When this occurs the body shifts to alternate fuel sources, such as for example proteins. The proteins are catabolized to restore ATP production by the oxidation of amino acids. The cellular conditions during proteolysis cause the activation of glutamine synthetase (GS). The activation of GS occurs, for example, in energy deficient disorders such as diabetes mellitus, hypertension and cyanide poisoning.

Ingested cyanide is converted to thiocyanate by the body. The reaction of thiocyanate and hydroxylamine, when present in unacceptably high amounts, causes a proteolytic state that parallels the energy deficient diabetic state. This additional mechanism permits the metabolism of thiocyanate to help compensate energy deficiency in the cell. Hydrolysis of thiocyanate is an additional source of hydroxylamine which drives the GS reaction.

It is postulated that the color reaction and electropotential change observed by use of the present reagent which indicates an atherogenic metabolic state occurs when the reagent contacts intermediates of the GS catalyzed conversion of glutamine to S-y-glutamyl hydroxamate and $NH_3$ and hydroxyamine N-thiocarboxylate from the hydrolysis of thiocyanate.

A great increase in activity of GS and degradation of thiocyanate occurs in the saliva of the human suffering from atherogenic metabolism and therefore the reagent can be used for contact with saliva to determine the degree of atherogenic metabolic disturbance. In animals the reagent is most useful for contact with urine to determine the degree of atherogenic metabolic disturbance. Where the reagent is to be used for determination of a pathology of the liver by detecting bilirubin, the reagent is contacted with any body fluid and preferably urine or saliva of humans or animals.

In one embodiment, the reagent containing gelatin, $Fe^{3+}$, $Cl^-$, an aliphatic alcohol and calcium, sodium, potassium, nitrate, sulfate, phosphate, copper, zinc, $Fe^{2+}$, lead and arsenic is applied to a carrier and is mounted to a diagnostic strip of which is useful for detecting atherogenic metabolic disturbances and bilirubinemia by a color reaction.

It is postulated that the $Fe^{3+}$ gives the color reaction while the chloride ions and trace elements, it is postulated, maintain the real activity of the glutamine synthetase and the accuracy of registration of level of metabolic disturbances. It is further postulated that the alcohol ensures the sensitivity and the speed of the reaction. The gelatin appears to stabilize the whole system. It has been found that the gelatin prevents oxidation of the reagent on contact with air, creates an even distribution of the color on the surface of the carrier, which in turn allows for spectrometric examination, for example by use of a light glucometer, if desired, and ensures the speed, the reproducibility and the stability of the calorimetric reaction.

The gelatinous reagent contains about 0.05 to 6.0M chloride ions, about 0.05 to 5.5M aliphatic alcohol, about 0.015 to 4.0M $Fe^{3+}$ ions and at least trace amounts of calcium, sodium, potassium, nitrate, sulfate, phosphate, copper, zinc, $Fe^{2+}$, lead and arsenic. The reagent is preferably prepared using 0.083 to 0.15% gelatin by weight. The chloride ions are preferably from addition of sodium chloride, potassium chloride or a combination thereof. The aliphatic alcohol is preferably a polyalcohol and is selected from glycerol or ethylene glycol. The ferric ions are preferably from addition of ferric chloride, ferric nitrate or ferric sulfate salts and most preferably from a salt, such as ferric chloride hexahydrate, which contains at least trace amounts of the elements, for example (by weight) at least 0.05% calcium; at least 0.03% sodium; at least 0.02% potassium; at least 0.01% each of nitrate and sulfate; at least 0.01% each of phosphate, copper and zinc; at least 0.003% each of $Fe^{2+}$ and lead; and at least 0.0003% arsenic.

In a preferred embodiment, the reagent comprises an aqueous solution containing 0.083% to 0.093% gelatin by weight, 0.05 to 0.1M glycerol or ethylene glycol, 0.93 to 1.83M ferric ions from the addition of ferric chloride hexahydrate and an additional 0.05 to 0.1M chloride ions from the addition sodium chloride and potassium chloride and trace amounts of calcium, sodium, potassium, nitrate, sulfate, phosphate, copper, zinc, $Fe^{2+}$, lead and arsenic. Preferably, the ferric chloride hexahydrate is selected to contain sufficient amounts of the trace agents, for example (by weight): at least 0.05%, and preferably 0.05% to 0.1%, calcium; at least 0.03%, and preferably 0.03 to 0.1%, sodium; at least 0.02%, and preferably 0.02 to 0.05%, potassium; at least 0.01%, and preferably 0.01 to 0.03%, each of nitrate and sulfate; at least 0.01%, and preferably 0.01 to 0.02%, each of phosphate, copper and zinc; at least 0.003%, and preferably 0.003 to 0.005% each of $Fe^{2+}$ and lead; and at least 0.0003%, and preferably 0.0003 to 0.0005%, arsenic.

The gelatinous reagent solution is applied to a suitable carrier material such as, for example, cellulosic materials, or suitable glass or plastic fibre materials. The solution can be applied to the carrier in any suitable way. The impregnated carrier material is thereafter dried. The impregnated carrier matrix can then be affixed to an insoluble support member, such as a plastic strip, by suitable means, such as two-sided tape. Of course, the matrix can be first affixed to the support member and thereafter impregnated, as would be understood.

In use, the reagent carrying portion of the strip is placed in a sample of human saliva or animal urine for a short period of time, for example 1 to 2 seconds. After contact a color reaction develops completely in 40 to 60 seconds allowing visual observation and diagnosis.

The color forming reagent forms a color spectrum which ranges from yellow, through orange, red, brown, black, and green. The colors which develop upon contact of the reagent with human saliva are as listed in Table I, where color indications having the superscripts "+" indicate the deepness of the shade.

TABLE I

| Color | CONDITION |
|---|---|
| yellow, orange | normal metabolism |
| orange+, red | moderate or moderate-serious atherogenic metabolism eg. low cyanide toxicity, hypertension, early type 2 diabetes, Syndrome-X |
| red+, red++, red+++ | serious atherogenic metabolism eg. types 1 and 2 diabetes, Syndrome-X or such conditions not effectively controlled by therapeutic measures |
| brown, black | more serious atherogenic metabolism eg. heavy cyanide toxicity, ketoacidosis |
| green, green+, green+++ | bilirubinemia |

In animals, the color indication is reversed wherein black indicates a normal animal and yellow indicates a diseased animal. It is postulated that the levels of the marker products for the test strip released through the urine is greater in healthy animals than in animals suffering from atherogenic metabolism. A green colorimetric reaction in animals indicates that the animal is suffering from bilirubinemia from a serious pathology of the liver.

In another embodiment, the reagent of the present invention is used with another reagent on a diagnostic strip which detects atherogenic metabolic disturbances and bilirubinemia by measuring the electropotential of the reagents when in contact with a body fluid from a subject under examination. The strip carries two reagents which react with the body fluid to create an electropotential between two electrodes. The first gelatinous reagent contains about 0.05 to 6.0M chloride ions, about 0.05 to 5.5M aliphatic alcohol, 0.015 to 1.85M $Fe^{3+}$ and at least trace amounts of calcium, sodium, potassium, nitrate, sulfate, phosphate, copper, zinc, $Fe^{2+}$, lead and arsenic. The second gelatinous reagent contains 3.0 to 4.0M oxammonium sulfate, $(NH_2OH)_2H_2SO_4$. The reagents can contain 0.083 to 0.15% gelatin by weight. The chloride ions are preferably from addition of sodium chloride, potassium chloride or a combination thereof. The aliphatic alcohol is preferably an aliphatic polyol such as glycerol or ethylene glycol. The ferric ions are preferably from addition of a ferric salt such as ferric chloride, ferric nitrate or ferric sulfate and most preferably from a salt, such as ferric chloride hexahydrate, which contains at least trace amounts of the elements, for example (by weight) at least 0.05% calcium; at least 0.03% sodium; at least 0.02% potassium; at least 0.01% each of nitrate and sulfate; at least 0.01% each of phosphate, copper and zinc; at least 0.003% each of $Fe^{2+}$ and lead; and at least 0.0003% arsenic.

In a preferred embodiment, the strip carries a first reagent formed of an aqueous solution of 0.083% to 0.093% gelatin by weight, 0.05 to 0.1M glycerol or ethylene glycol, 0.93 to 1.83M ferric ions from the addition of ferric chloride hexahydrate and an additional 0.05 to 0.1M chloride ions from the addition sodium chloride and potassium chloride and trace amounts of calcium, sodium, potassium, nitrate, sulfate, phosphate, copper, zinc, $Fe^{2+}$, lead and arsenic. Preferably the ferric chloride hexahydrate is selected to contain the appropriate amounts of the trace elements, as listed hereinbefore with reference to the strip of the first embodiment.

The second reagent is preferably an aqueous solution of 0.083 to 0.093% gelatin by weight and 3.0 to 4.0M oxammonium sulfate. The first and second gelatinous reagents are applied, in any suitable way to suitable carriers. Drying time is permitted and the carriers are then attached to an insoluble, support member. Two carriers, one impregnated with the first reagent and the second carrier impregnated with the second reagent, are applied to each strip in a close arrangement that allows a body fluid sample to come into contact with both reagents and to allow access by electropotential measuring electrodes.

In one embodiment, the electrodes are mounted on the strip and the electropotential is measured with a glucometer, such as an Elite™ glucometer available from Bayer Inc.

In use, a sample of human saliva or animal urine is applied to the strip so that it comes into contact with both carriers. After a suitable period of time, for example 60 seconds, the electropotential is measured and compared against standards or an established chart of electropotential reading. The electropotential indicates the level of atherogenic metabolism or the presence of levels of bilirubin in the sample which would indicate an occurrence of bilirubinemia.

Using the strip of the preferred embodiment, electropotential readings have been obtained from human saliva as shown in Table 2.

TABLE 2

| CONDITION | ELECTROPOTENTIAL (mV) |
|---|---|
| true normal | 0–6 |
| moderate to moderate-serious atherogenic metabolism eg. Syndrome-X, low cyanide toxicity, hypertension, early type 2 diabetes | 6–8.5 |
| serious atherogenic metabolism eg. type 1 and 2 diabetes, Syndrome-X or such disorders not effectively controlled by therapeutic measures | 10–22 |
| more serious atherogenic metabolism eg. heavy cyanide toxicosis, kefoacidosis | 21–30 |
| bilirubinemia | 15–25 |

In animals, the electropotential results are reversed from those obtained from humans with true normal being indicated by a reading of 21–30 mV and a diabetic animal sample giving a reading of 0–6 mV.

In laboratory examination, the level of atherogenic metabolism can be determined by spectrometer or colorimeter analysis using the gelatinous reagent containing ferric and chloride ions, aliphatic alcohol and the trace agents. For this analysis, the saliva or urine sample is prepared first by centrifugation treatment at 12,000 g for 1 to 1.5 minutes. After centrifugation, 520 to 600 ml of the supernatant is mixed with 190 to 250 ml of the reagent solution until an even color is obtained. This mixture is then centrifuged again, as described above. 500 ml of the supernatant is extracted and mixed in a 1:3 volume ratio with TRIS-NaCl buffer at pH 7.42 to 7.43. The optical density of this mixture is then analyzed using a spectrophotometer at 540 nm and 480 nm and comparison is made against standards.

The strip of the present invention can be used alone as a screening tool. The strip will identify a subject having atherogenic metabolism or bilirubinemia. In addition, the strip can be used as a monitoring tool for following a subject having known atherogenic metabolism, such as a diagnosed diabetic, to determine the effectiveness of therapeutic measures. The strip can be used in combination with other tests, such as the glucose and HbAIC tests, which will assist in the specific identification of a disorder.

BRIEF DESCRIPTION OF THE DRAWINGS

A further, detailed, description of the invention, briefly described above, will follow by reference to the following drawings of specific embodiments of the invention. These drawings depict only typical embodiments of the invention and are therefore not to be considered limiting of its scope. In the drawings.

DETAILED DESCRIPTION OF THE PREFERRED EMBODIMENTS

Figure 1:
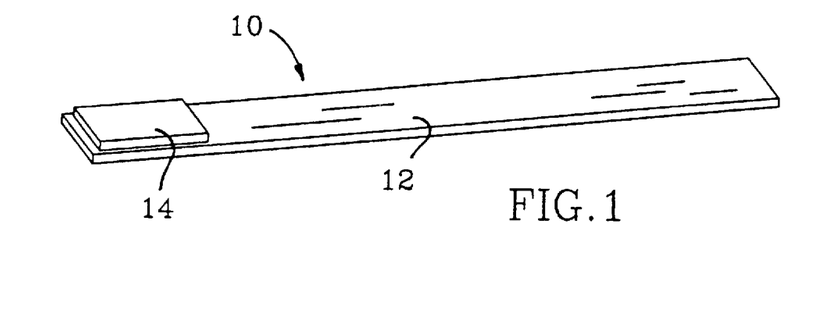
FIG. 1 is a perspective view of a calorimetric diagnostic strip according to the present invention.

Referring to FIG. 1, a colorimetric diagnostic strip 10 is shown according to the present invention. Strip 10 includes an insoluble support member 12 which is preferably formed of white plastic material. Support member 12 has adhesively secured thereon, a filter paper carrier 14 impregnated with reagent. The reagent is preferably an aqueous solution containing 0.083% to 0.093% gelatin by weight, 0.05 to 0.1M glycerol or ethylene glycol, 0.93 to 1.83M ferric ions from the addition of ferric chloride hexahydrate and an additional 0.05 to 0.1M chloride ions from the addition sodium chloride and potassium chloride and at least trace amounts of calcium, sodium, potassium, nitrate, sulfate, phosphate, copper, zinc, $Fe^{2+}$, lead and arsenic. Preferably, the ferric chloride hexahydrate is selected to contain the trace agents in suitable amounts, for example (by weight): at least 0.05%, and preferably 0.05% to 0.1%, calcium; at least 0.03%, and preferably 0.03 to 0.1%, sodium; at least 0.02%, and preferably 0.02 to 0.05%, potassium; at least 0.01%, and preferably 0.01 to 0.03%, each of nitrate and sulfate; at least 0.01%, and preferably 0.01 to 0.02%, each of phosphate, copper and zinc; at least 0.003%, and preferably 0.003 to 0.005% each of $Fe^{2+}$ and lead; and at least 0.0003%, and preferably 0.0003 to 0.0005%, arsenic. The reagent is applied to carrier 14 and permitted time to dry prior to securing carrier 14 onto member 12.

Strip 10 is used to determine the degree of atherogenic metabolism or bilirubinemia by observation of a calorimetric reaction which occurs when carrier 14 is brought into contact with human saliva or animal urine. Preferably, carrier 14 is immersed in the sample for a short period of time, for example one to two seconds. The calorimetric reaction develops in 40 to 60 seconds and can be yellow, orange, red, brown, black or green, as discussed hereinbefore.

Figure 2A:
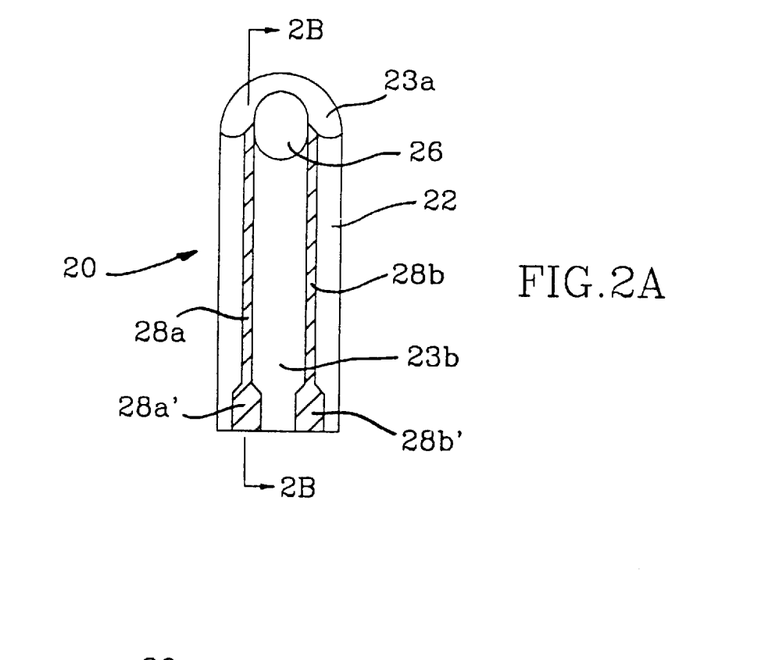
FIG. 2A is a plan view of an electropotential diagnostic strip according to the present invention.
Figure 2B:
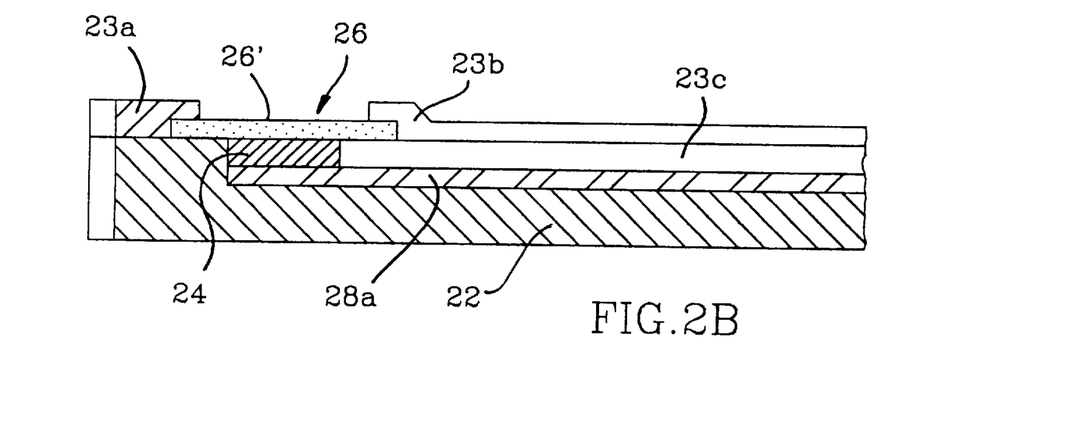
FIG. 2B is a sectional view along line 2B—2B of FIG. 2A.

Referring to FIGS. 2A and 2B, there is shown an electropotential diagnostic strip 20 according to the present invention. Strip 20 includes an insoluble support base member 22 and retaining members 23a, 23b, 23c. Members 22, 23a, 23b, 23c support and secure a first carrier 24, a second carrier 26 and electrodes 28a and 28b.

First carrier 24 is preferably filter paper and is impregnated with a first reagent which is preferably an aqueous solution containing 0.083% to 0.093% gelatin by weight, 0.05 to 0.1M glycerol or ethylene glycol, 0.93 to 1.83M ferric ions from the addition of ferric chloride hexahydrate and an additional 0.05 to 0.1M chloride ions from the addition sodium chloride and potassium chloride and trace amounts of calcium, sodium, potassium, nitrate, sulfate, phosphate, copper, zinc, $Fe^{2+}$, lead and arsenic. Preferably, the ferric chloride hexahydrate is selected to contain the elements in suitable amounts, for example (by weight): at least 0.05%, and preferably 0.05% to 0.1%, calcium; at least 0.03%, and preferably 0.03 to 0.1%, sodium; at least 0.02%, and preferably 0.02 to 0.05%, potassium; at least 0.01%, and preferably 0.01 to 0.03%, each of nitrate and sulfate; at least 0.01%, and preferably 0.01 to 0.02%, each of phosphate, copper and zinc; at least 0.003%, and preferably 0.003 to 0.005% each of $Fe^{2+}$ and lead; and at least 0.0003%, and preferably 0.0003 to 0.0005%, arsenic. The reagent is applied to carrier 24 and permitted time to dry prior to securing carrier 24 onto member 22.

Second carrier 26 is also preferably filter paper and is impregnated with a second reagent which is preferably an aqueous solution of 0.083 to 0.093% gelatin by weight and 3.0 to 4.0M oxammonium sulfate. This reagent is applied to carrier 26 and permitted time to dry prior to placing carrier 26 onto carrier 24 and securing the carrier with retaining members 23a, 23b, 23c.

Electrodes 28a and 28b are in contact with carrier 24 at their first ends and are shaped at their opposite ends 28a', 28b' to contact the mating electrodes of a glucometer, as is known.

Strip 20 is used to determine the degree of atherogenic metabolism or bilirubinemia by measuring the electropotential generated when a sample of human saliva or animal urine is brought into contact with the carriers 24, 26. The sample is placed on exposed surface 26' of carrier 26. The sample passes into carrier 26 and in turn into carrier 24. After a suitable period, for example 60 seconds, the electropotential is measured and analyzed as discussed hereinbefore.

The invention will be further illustrated by the following examples. While the examples illustrate the invention, they are not intended to limit the scope of the invention.

EXAMPLE 1

Diagnostic strips were prepared according to the following method: Ferric chloride hexahydrate was treated by repeated cycles of dissolution and crystallization to contain (by weight) 0.1% each of calcium and sodium, 0.5% potassium, 0.03% each of nitrate and sulfate, 0.02% each of phosphate copper and zinc, 0.005% each of $Fe^{2+}$ and lead and 0.0005% of arsenic.

A physiological aqueous reagent solution was prepared containing 0.083% gelatin by weight, 0.05M glycerol, 1.83M ferric ions from the addition of the prepared ferric chloride hexahydrate and an additional 0.05M chloride ions from the addition sodium chloride and potassium chloride.

The aqueous reagent was applied to filter paper and allowed to dry. The paper was applied to a white plastic support and the assembly was cut into strips.

Saliva samples were collected from 55 true normal individuals. True normal individuals are those who are taking no medications, do not smoke and have been determined by traditional tests to have no medical disorders.

Prepared strips were immersed in each saliva sample for two seconds and then set aside for 60 seconds. The developed color was recorded for each sample and the results are shown in Table 3.

TABLE 3

| % INDIVIDUALS | COLORIMETRIC ANALYSIS |
|---|---|
| 90.9% | Yellow to Orange |
| 9.1% | Red+ |

Thus, for over 90% of the subjects, the analysis showed a yellow to orange result. This was considered as a normal result for the purposes of the test. Up to about 10% of the results, however, based on this study, could be false positives or could be individuals who suffer from atherogenic metabolism which is not detected by traditional tests.

EXAMPLE 2

Using the test strips and method as described in Example 1, 140 apparently healthy subjects were screened and seven were found to have a $R^+$ to $R^{+++}$ colorimetric result. The results of traditional oral glucose tolerance and immunoreactive insulin tests for the seven subjects are presented in Table 4.

TABLE 4

| | Glucose level (mmol/l) | | | immunoreactive insulin (u unit/ml) | | |
|---|---|---|---|---|---|---|
| Subject No. | Orig. level | 1 hour later | 2 hrs later | orig. level | 1 hr later | 2 hrs later |
| 1 | 4.8 | 11.6 | 8.0 | 34 | 160 | 120 |
| 2 | 5.2 | 8.8 | 8.3 | 150 | 95 | 88 |
| 3 | 5.8 | 8.1 | 9.4 | 86 | 63 | 114 |
| 4 | 4.1 | 7.9 | 4.5 | 67 | 94 | 18 |
| 5 | 5.2 | 11.8 | 10.6 | — | 120 | 132 |
| 6 | 5.7 | 8.2 | 6.4 | 36 | 96 | 2 |
| 7 | 5.3 | 7.9 | 6.6 | | | |

The tests showed that all subjects, except subject #4, appeared to be glucose intolerant or insulin resistant. Further clinical tests showed that subjects #3 and #5 were diabetic.

EXAMPLE 3

Figure 3A:
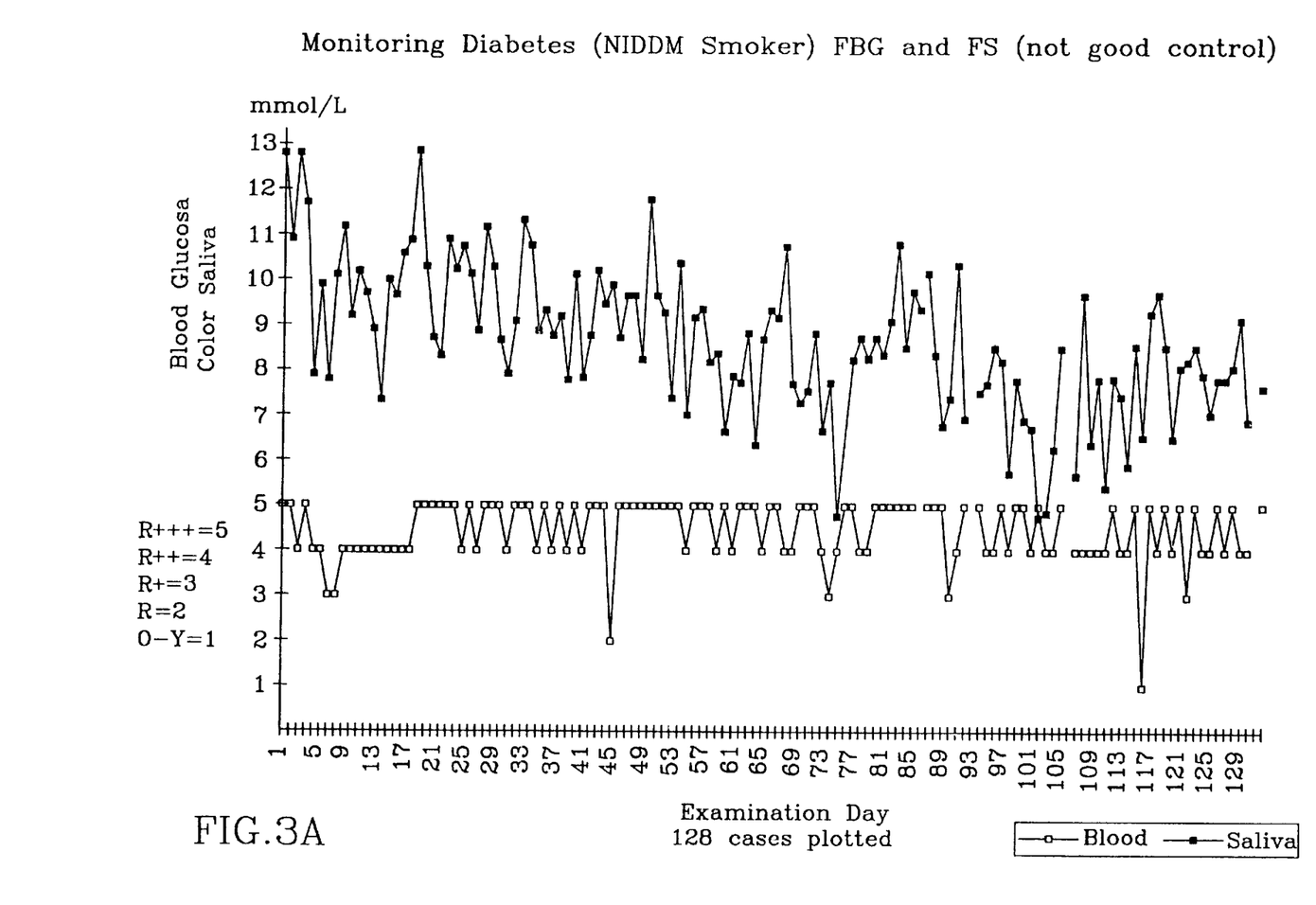
FIG. 3A is a chart of colorimetric analysis, using the diagnostic strip of the present invention, and glucose blood levels, using traditional analysis, versus the examination day of a subject having diabetes with poor control.

A patient was monitored over a period of 128 days using a fast blood glucose test and the diagnostic strip of the present invention (using the strip and method as described in Example 1). The patient had non-insulin dependent diabetes mellitus and smoked heavily (ie. more than 10 cigarettes/day). The patient was undergoing treatment for diabetes but was not found to have good control. The results are shown in FIG. 3A. While the blood glucose levels varied widely, the saliva tests showed with high sensitivity the fluctuations in the level of atherogenic metabolism and thereby cellular energy deficiency which are characteristic of a type 2 diabetic without good control.

Figure 3B:
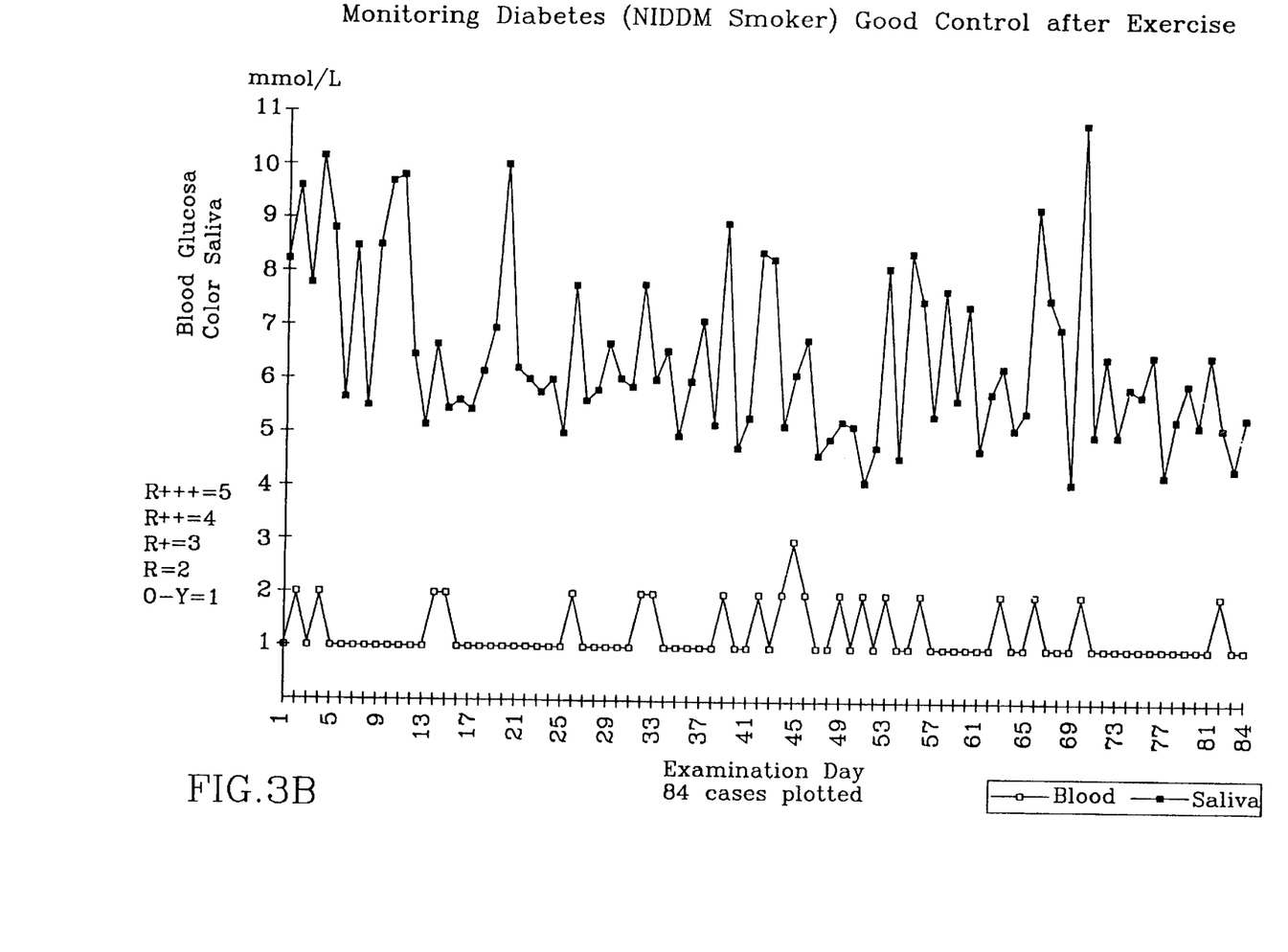
FIG. 3B is a chart of colorimetric analysis, using the diagnostic strip of the present invention, and glucose blood levels, using traditional analysis, versus the examination day of a subject having diabetes with good control; and, FIG. 4 is a chart of an analysis of 95 saliva samples comparing the results obtained from the calorimetric strip and the electropotential strip.

A second patient was monitored over a period of 84 days using a fast blood glucose test and the diagnostic strip test of the present invention (using the strip and method as described in Example 1). The patient had non-insulin dependent diabetes mellitus and smoked cigarettes (ie. more than 10 cigarettes/day). A treatment regime of about 1 hour 40 minutes daily exercise was found to have excellent results in terms of control of the atherogenic metabolism associated with the diabetes and smoking. The results are shown in FIG. 3B. The colorimetric results confirm that the treatment program is providing good control of the disorder. Further, the results show that the level atherogenic metabolism is being monitored by the test and the fact that the subject continues to smoke heavily has no effect on the results of the test.

EXAMPLE 4

300 Saliva samples were obtained from patients having poorly controlled non-insulin dependent diabetes mellitus. Each sample was analyzed by two methods.

The first method is as follows: Ferric chloride hexahydrate was treated by repeated cycles of dissolution and crystallization to contain (by weight) 0.03% insoluble substances, 0.01% each of nitrate, sulfate, copper, zinc and phosphate, 0.5% calcium, 0.03% of sodium, 0.02% of potassium, 0.003% each of $Fe^{2+}$ and lead and 0.0003% of arsenic.

An aqueous reagent solution for use in the first method was prepared containing 0.1M glycerol and 0.05M ferric ions from the addition of the prepared ferric chloride hexahydrate and an additional 0.05M chloride ions from the addition sodium chloride and potassium chloride.

Using the saliva samples and the prepared reagent solution, 25 μL reagent was mixed with 50 μL of saliva. The color change was observed and recorded.

The second method was according to the strips and method of Example I, except a concentration of 0.08M glycerin was used.

The results are shown in Table 5.

TABLE 5

| METHOD # | CORRECT RESULTS (%) | FALSE POSITIVE (%) | FALSE NEGATIVE (%) |
|---|---|---|---|
| 1 | 85 | 10.3 | 4.2 |
| 2 | 97.3 | 2 | 0.7 |

EXAMPLE 5

Using 95 saliva samples collected from true normal and diabetic individuals two methods were compared.

The first method is as follows:

An aqueous solution of 0.083% gelatin and 3.0M oxammonium sulfate was prepared and applied to filter paper. The filter paper was dried.

A second aqueous solution containing 0.083% gelatin by weight, 0.08M glycerol, 0.03M $Fe^{3+}$ ions from the addition of ferric chloride hexahydrate containing (by weight) 0.1% each of calcium and sodium, 0.5% potassium, 0.03% each of nitrate and sulfate, 0.02% each of phosphate copper and zinc, 0.005% each of $Fe^{2+}$ and lead and 0.0005% of arsenic and an additional 0.05M chloride ions from addition of sodium chloride and potassium chloride. This solution was also applied to filter paper and allowed to dry.

The impregnated papers were used to produce strips as shown in FIGS. 2A and 2B.

The strips were used for saliva analysis by placing the strip in the glucometer and placing a drop of saliva on the exposed surface of the impregnated paper of the strip and recording the electropotential registered by the glucometer. The glucometer used was Elite™, by Bayer Inc.

The second method was according to Example 1.

Figure 4:
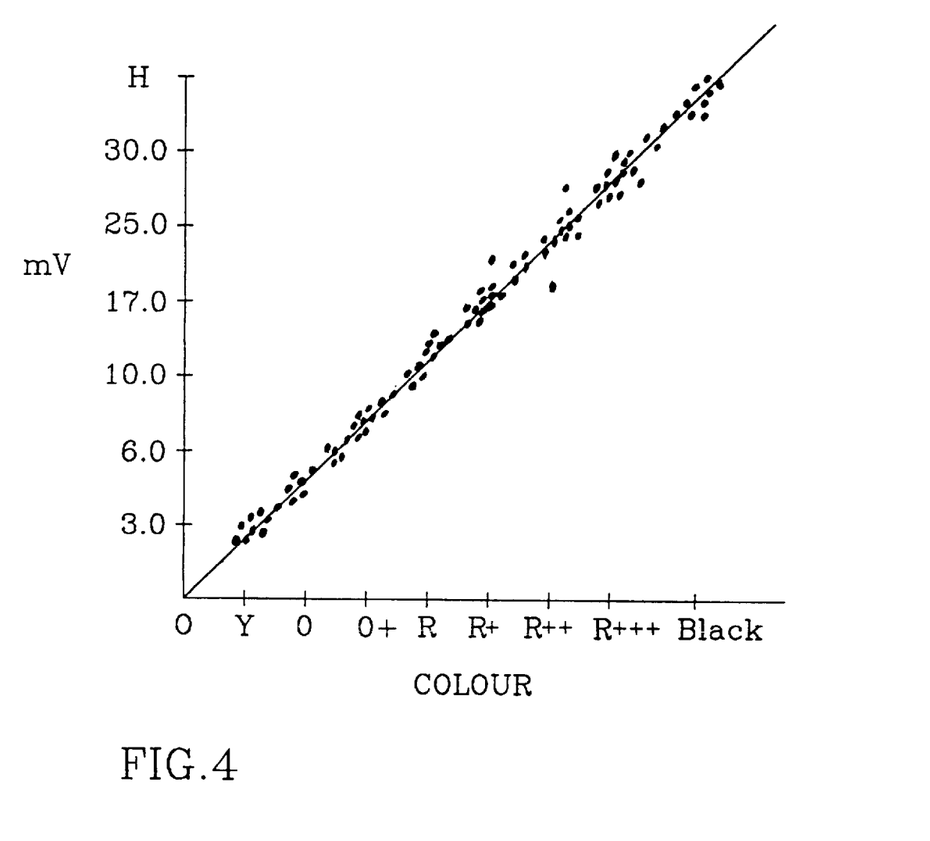

The results of the tests for the 95 samples are shown in FIG. 4.

EXAMPLE 6

Five true normal patients (TN1 to TN5), eight diabetic patients having type I or type II diabetes (DI1 to DI3 and DII1 to DII5) and five patients having bilirubinemia (B1 to B5) were analyzed using the method of Example 5. The concentration of bilirubin in the blood serum of patients B1 to B5 was also determined.

The results are shown in Table 6 where Y=yellow, O=orange, R=red and G=green.

TABLE 6

| PATIENT NO. # | BILIRUBIN IN SERUM (mg/100 ml) | COLORIMETRIC RESULT | ELECTRO-POTENTIAL RESULT (mV) |
|---|---|---|---|
| TN1 | — | Y | 2.5 |
| TN2 | — | O | 4.8 |
| TN3 | — | O | 5.0 |
| TN4 | — | Y | 2.7 |
| TN5 | — | O | 5.1 |
| DII 1 | — | $O^+$ | 7.5 |
| DII 2 | — | R | 8.0 |
| DII 3 | — | $R^+$ | 10 |
| DI 1 | — | $O^+$ | 7.0 |
| DI 2 | — | $R^{++}$ | 15.0 |
| DII 4 | — | $R^{++}$ | 15.5 |
| DII 5 | — | $R^{+++}$ | 22.0 |
| DI 3 | — | $R^+$ | 11.0 |
| B1 | 1.2 | G | 15 |
| B2 | 2.5 | $G^+$ | 17 |
| B3 | 3.6 | $G^{++}$ | 20 |
| B4 | 5 | $G^{+++}$ | 22 |
| B5 | 17 | $G^{+++}$ | 25 |

EXAMPLE 7

Using the method of Example 5 (except that urine samples were used in place of the saliva), five true normal rats (TN1 to TN5) and five rats having bilirubinemia (B1 to B5) were analyzed. The concentration of bilirubin in the blood serum of rats B1 to B5 was also determined.

The results are shown in Table 7.

TABLE 7

| RAT # | SERUM BILIRUBIN (mg/100 ml) | COLORIMETRIC RESULT | ELECTRO-POTENTIAL (mV) |
|---|---|---|---|
| TN1 | — | Brown | 30.0 |
| TN2 | — | $R^{+++}$ | 25.0 |
| TN3 | — | $R^{+++}$ | 23.0 |
| TN4 | — | Dark Brown | 39.0 |
| TN5 | — | Dark Brown | 28.0 |
| B1 | 2.0 | $green^+$ | 2.0 |
| B2 | 2.9 | $green^{++}$ | 3.0 |
| B3 | 4.5 | $green^{+++}$ | 5.0 |
| B4 | 5 | $green^{+++}$ | 7.0 |
| B5 | 5 | $green^{+++}$ | 7.0 |

EXAMPLE 8

Using the method of Example 5 (except that urine samples were used in place of the saliva), five rats diagnosed as having diabetes were treated by transplantation of the islets of Langerhans. The animals were tested within two weeks of transplantation, between one and two months after transplantation and between three and four months after transplantation. The results are shown in Table 8.

TABLE 8

| TIME | COLOR TEST | ELECTROPOTENTIAL TEST (mV) |
|---|---|---|
| within two weeks | | |
| rat 1 | O | 4.5 |
| rat 2 | R | 6.2 |
| rat 3 | $O^+$ | 6.0 |
| rat 4 | R | 6.5 |
| rat 5 | $O^+$ | 5.9 |
| bet. 1 and 2 months | | |
| rat 1 | $R^+$ | 10.0 |
| rat 2 | $R^{++}$ | 17.0 |
| rat 3 | $R^{++}$ | 17.0 |
| rat 4 | $R^+$ | 12.0 |
| rat 5 | $R^+$ | 11.0 |
| bet. 3 and 4 months | | |
| rat 1 | $R^{+++}$ | 26.0 |
| rat 2 | $R^{+++}$ | 23.0 |
| rat 3 | Dark Brown | 27.0 |
| rat 4 | Dark Brown | 30.0 |
| rat 5 | Dark Brown | 29.0 |

It will be apparent that changes may be made to the illustrative embodiments, while falling within the scope of the invention and it is intended that all such changes be covered by the claims appended hereto.

We claim:

1. A diagnostic strip carrying a carrier matrix impregnated with a gelatinous reagent for diagnostic determination comprising 0.083 to 0.15% by weight gelatin, about 0.05 to 6.0M chloride ions, about 0.05 to 5.5M aliphatic alcohol, 0.015 to 4.0M $Fe^{3+}$ from a ferric salt and 0.05% to 0.1% calcium, 0.03 to 0.1% sodium, 0.02 to 0.05% potassium, 0.01 to 0.03%, each of nitrate and sulfate, 0.01 to 0.02%, each of phosphate, copper and zinc, 0.003 to 0.005% each of $Fe^{2+}$ and lead; and 0.0003 to 0.0005% arsenic, all by weight.

2. The diagnostic strip of claim 1 wherein the carrier matrix is formed of paper and the strip is formed of a water insoluble material.

3. The diagnostic strip of claim 1 wherein in the gelatinous reagent the aliphatic alcohol is a polyalcohol selected from the group consisting of glycerol and ethylene glycol and is present at a concentration of 0.05 to 0.1M, the ferric ions are from the addition of ferric chloride hexahydrate and are present at a concentration of 0.93 to 1.83M and the chloride ions are in part from the addition sodium chloride and/or potassium chloride at a concentration of 0.05 to 0.1M.

4. A diagnostic strip carrying a first carrier matrix and a second carrier matrix, the first carrier matrix impregnated with a first gelatinous reagent for diagnostic determination comprising:

0.083 to 0.15% by weight gelatin, about 0.05 to 6.0M chloride ions, about 0.05 to 5.5M aliphatic alcohol, 0.015 to 1.85M $Fe^{3+}$ ions from a ferric salt and 0.05% to 0.1% calcium, 0.03 to 0.1% sodium, 0.02 to 0.05% potassium, 0.01 to 0.03%, each of nitrate and sulfate, 0.01 to 0.02%, each of phosphate, copper and zinc, 0.003 to 0.005% each of $Fe^{2+}$ and lead; and 0.0003 to 0.0005% arsenic, all by weight; and the second carrier matrix impregnated with a second gelatinous reagent for diagnostic determination comprising 0.083 to 0.15% by weight gelatin, about 3.0 to 4.0M oxammonium sulfate, the first and second carriers being positioned in close proximity on the strip.

5. The diagnostic strip of claim 4 wherein in the first gelatinous reagent the aliphatic alcohol is a polyalcohol selected from the group consisting of glycerol and ethylene glycol and is present at a concentration of 0.05 to 0.1M, the ferric ions are from the addition of ferric chloride hexahydrate and are present at a concentration of 0.93 to 1.83M and the chloride ions are in part from the addition sodium chloride and/or potassium chloride at a concentration of 0.05 to 0.1M.

6. The diagnostic strip of claim 4 wherein the second carrier matrix is positioned on top of the first carrier matrix.

* * * * *